United States Patent
Bourquin et al.

(10) Patent No.: US 11,471,093 B2
(45) Date of Patent: Oct. 18, 2022

(54) SYSTEM FOR MILK EJECTION REFLEX DETERMINATION

(71) Applicant: KONINKLIJKE PHILIPS N.V., Eindhoven (NL)

(72) Inventors: Yannyk Parulian Julian Bourquin, Eindhoven (NL); Lili-Marjan Brockhuis, Geldrop (NL); Łucja Elżbieta Segaar, Eindhoven (NL); Jozef Hubertus Gelissen, Herten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 479 days.

(21) Appl. No.: 16/612,816

(22) PCT Filed: May 10, 2018

(86) PCT No.: PCT/EP2018/062163
§ 371 (c)(1),
(2) Date: Nov. 12, 2019

(87) PCT Pub. No.: WO2018/210685
PCT Pub. Date: Nov. 22, 2018

(65) Prior Publication Data
US 2020/0146613 A1    May 14, 2020

(30) Foreign Application Priority Data
May 17, 2017    (EP) .................... 17171544

(51) Int. Cl.
*A61B 5/00*    (2006.01)
*A61M 1/06*    (2006.01)
(Continued)

(52) U.S. Cl.
CPC .......... *A61B 5/4312* (2013.01); *A61B 5/0082* (2013.01); *A61B 5/01* (2013.01);
(Continued)

(58) Field of Classification Search
CPC ........ A61M 1/06; A61M 1/062; A61M 1/069; A61M 1/0693; A61M 1/06935
See application file for complete search history.

(56) References Cited

U.S. PATENT DOCUMENTS

| 8,376,986 B2 | 2/2013 | Van Schijndel |
| 8,597,234 B2 | 12/2013 | Larsson |

(Continued)

FOREIGN PATENT DOCUMENTS

| EP | 2277571 | 1/2011 |
| WO | 00/57934 | 10/2000 |

(Continued)

OTHER PUBLICATIONS

Prime et al., Using milk flow rate to investigate milk ejection in the left and right breasts during simultaneous breast expression in women. International Breastfeeding Journal 2009, 4:10 (Year: 2009).*

(Continued)

*Primary Examiner* — Emily L Schmidt

(57) ABSTRACT

The present invention relates to a system, method and corresponding computer program for milk ejection reflex (MER) determination, the system comprising a breast shield arrangement (1) for a breast pump (2) configured to be attached on a first breast of a female, a physiological sensor unit (4) for receiving a physiological reception signal from the second breast, which is opposite to the first breast, wherein the physiological reception signal is indicative of fluid contents in the second breast, and wherein the system is configured to determine a milk ejection reflex based on a change in fluid contents in the second breast. It finds particular application during and in connection with breastfeeding and allows for direct detection of the beginning of the milk flow in the breast, i.e. the occurrence of the MER, without delay and with a high degree of precision.

20 Claims, 3 Drawing Sheets

(51) Int. Cl.
*A61B 5/01* (2006.01)
*A61B 5/0537* (2021.01)

(52) U.S. Cl.
CPC .......... *A61B 5/0537* (2013.01); *A61B 5/6802* (2013.01); *A61B 5/6898* (2013.01); *A61M 1/066* (2014.02); *A61M 2205/3303* (2013.01); *A61M 2205/3306* (2013.01); *A61M 2205/3334* (2013.01); *A61M 2205/3344* (2013.01); *A61M 2205/502* (2013.01); *A61M 2205/581* (2013.01); *A61M 2205/582* (2013.01); *A61M 2230/06* (2013.01)

(56) References Cited

U.S. PATENT DOCUMENTS

| | | | |
|---|---|---|---|
| 9,173,587 B2 | 11/2015 | Van Schijndel | |
| 2005/0059928 A1* | 3/2005 | Larsson | A61M 1/06 600/382 |
| 2008/0076991 A1* | 3/2008 | Ayers | A61B 5/4821 600/324 |
| 2008/0077042 A1 | 3/2008 | Feldkamp | |
| 2014/0171917 A1* | 6/2014 | Greter | A61M 1/75 604/514 |
| 2016/0157725 A1* | 6/2016 | Munoz | H04N 5/2256 600/407 |
| 2016/0220743 A1 | 8/2016 | Guthrie | |
| 2016/0287767 A1* | 10/2016 | Simmons | A61M 1/06 |

FOREIGN PATENT DOCUMENTS

| | | |
|---|---|---|
| WO | 2010/029483 | 3/2010 |
| WO | 2013/093739 | 6/2013 |
| WO | 2017/080851 | 5/2017 |

OTHER PUBLICATIONS

International Search Report and Written Opinion dated Jul. 20, 2018 for International Application No. PCT/EP2018/062163 Filed May 10, 2018.
http://www.who.int/topics/breastfeeding/en/.
Michael W. Woolridge, "The 'anatomy'of infant sucking", Midwifery, (1986) 2, 164-171.

* cited by examiner

SYSTEM FOR MILK EJECTION REFLEX DETERMINATION

CROSS REFERENCE TO RELATED APPLICATIONS

This application is the U.S. National Phase application under 35 U.S.C. § 371 of International Application No. PCT/EP2018/062163 filed May 10, 2018, published as WO 2018/210685 on Nov. 22, 2018, which claims the benefit of European Patent Application Number 17171544.4 filed May 17, 2017. These applications are hereby incorporated by reference herein.

FIELD OF THE INVENTION

The present invention relates to a system, method and corresponding computer program for milk ejection reflex (MER) determination. It finds particular application during and in connection with breastfeeding. The invention is however not limited to this application.

BACKGROUND OF THE INVENTION

WO 00/57934 A1 discloses a mammary gland pump for extracting breast milk from a female breast. The mammary gland pump comprises a receiving unit configured to receive a breast therein. The receiving unit is in suction communication with a vacuum source, the suction being controlled by a micro-processor controlled electromechanical valve for simulating natural suckling patterns, especially suckling patterns stimulating the milk ejection reflex (MER).

If breastfeeding is carried out, the baby's suckling pattern will trigger the MER, but if a mammary gland pump has to be used, the milk ejection might be not successful or not effective due to lack of correct suckling patterns. To aid the milk ejection, the teaching of WO 00/57934 A1 proposes to arrange a sensor in the receiving unit to detect the start of milk flow from the breast. The signal of the sensor is then fed back to the micro-processor which changes the respective suckling pattern from "triggering" to "emptying".

However, the sensor is arranged in optical communication with the coupling end of the receiving unit, that is, no MER can be detected but milk ejection is only detected when a fluid flow through the reception unit in vicinity to the sensor occurs. Due to the distance between mammary gland and sensor the detection of the milk flow and thus the adjustment of the suckling pattern are delayed. Besides, faulty measurements can occur when other fluids are present, for example sweat or water due to previous lavation of breast or receiving unit.

WO 2017 080851 A1 discloses a breast shield arrangement for a breast pump comprising a breast shield for receiving a user's breast therein, and a sensor for transmitting an input signal into the breast and receiving a corresponding reception signal in response, said reception signal indicating changes in milk flow in the breast.

EP 2 277 571 A1 discloses an apparatus comprising a sensing unit configured to detect a physiological response from a user of a breast pump and to trigger a change in an operation of the breast pump in dependence of the detected physiological response, the sensing unit being located separately from a funnel of the breast pump.

SUMMARY OF THE INVENTION

It is an object of the present invention to provide a system which allows for direct detection of the beginning of the milk flow in the breast, i.e. the occurrence of the MER, without delay and with a high degree of precision.

According to a first aspect, a system for milk ejection reflex determination is provided. The system comprises a breast shield arrangement for a breast pump configured to be attached on a first breast of a female, and a physiological sensor unit for receiving a physiological reception signal from the second breast. The physiological reception signal is indicative of fluid contents in the second breast. The system is configured to determine a MER based on a change in fluid contents in the second breast. The first breast, which is in the following also referred to as a lactating breast since milk expression due to the breast shield arrangement can be performed using the first breast, is thus the breast opposite to the second breast, which is in the following also referred to as a non-lactating breast since the breast shield arrangement is not attached thereto and it is—for instance at the respective time—not used for milk expression. It is obvious that a left and right breast of the female can be the first and second breast, respectively, depending on which of the two breasts the breast shield arrangement for expressing milk is attached to.

A start of milk flow in the breast tissue, corresponding to the MER, is advantageously determined by directly detecting a change in fluid contents of the breast tissue, even before milk is actually detectable outside the breast tissue. Further, since the physiological sensor unit receives the physiological reception signal from the second breast which is non-lactating, i.e. e.g. the breast to which the breast shield arrangement is not attached and which corresponds to the breast opposite to the lactating or first breast, the physiological reception signal is not suffering from noise induced by mechanical movement from, for instance, the breast pump. Accordingly, the physiological reception signal obtained yields information on the MER with high accuracy. The physiological reception signal is not altered by movement and the first MER, as well as all additional MERs occurring during milk expression, can be detected with a high degree of precision. Further, since the MER is directly determined, the suckling pattern can be adjusted without delay and thus before milk is actually flowing out of the nipple.

In an embodiment the physiological sensor unit is configured to transmit an input signal into the non-lactating breast and to receive a corresponding physiological reception signal from the non-lactating breast in response. Advantageously, the measuring accuracy of the physiological sensor unit can, dependent on the measuring principle, be increased by transmitting the input signal. However, depending on the measuring principle of the physiological sensor unit, the physiological sensor unit can either rely on a transmitted input signal before receiving a physiological reception signal or not.

In an embodiment the physiological sensor unit comprises a contact photoplethysmographic (PPG) sensor, which is configured to be arranged in contact with the skin of the breast or in close vicinity to the skin, in particular at a distance of less than 1 cm.

Contact PPG sensors are widely known and available at low cost. The PPG sensor may comprise a single LED with a particular wavelength or multiple LEDs with a combination of different wavelengths, preferably in the range from 400 nm to 1300 nm. The contact PPG sensor can be connected to rest of the system for milk ejection reflex determination using a standard wired or wireless connection. Preferentially, the contact PPG sensor is held in contact with the non-lactating breast by the user at the time during which the breast shield arrangement is attached to the opposite breast. In other embodiments, the contact PPG sensor can also comprise suitable attachment means for maintaining the PPG sensor attached to the breast, without the user having to support it. Thereby, a convenience of usage can be further improved.

It should be noted that the contact PPG sensor and also all of the additional or alternative measurement sensors discussed in the following allow a non-invasive and painless determination of the physiological reception signal.

In an embodiment the sensor unit comprises additionally or alternatively at least one of a laser speckle sensor, a thermal sensor, and a bio impedance sensor. While each of these measurement techniques allows a precise and straightforward reception of the physiological reception signal, the invention is not limited to these measuring techniques and alternative or additional techniques are contemplated by the skilled person.

In an embodiment the physiological sensor unit comprises a remote PPG sensor, in particular a camera.

The remote PPG sensor (rPPG), similar to a contact PPG sensor, allows the determination of a PPG reception signal, wherein the rPPG sensor can be provided at a larger distance from the user's breast. Preferably, the rPPG sensor is configured to sense both breasts and to determine the non-lactating breast out of the two sensed breasts. More precisely, the rPPG sensor, preferably the camera, can in one embodiment obtain an image of both breasts and determine, out of the two imaged breasts, the non-lactating breast. Preferably, image recognition algorithms recognizing the non-lactating breast can be used for this purpose, for instance by recognizing the breast shield arrangement or a head of a baby on the lactating breast.

In an embodiment the physiological sensor unit comprises an imaging component, in particular a camera, configured to carry out laser speckle imaging (LSI), thermal imaging, and so on. Expressed differently, where applicable, all measuring techniques can also be implemented in the form of a remote sensing technique instead of or in addition to the contact measuring technique. Variations in this respect are well-known to a person skilled in the art.

In an embodiment the physiological sensor unit is integrated into a smartphone.

Preferably, the physiological sensor unit integrated into the smartphone employs the smartphone's camera or a dedicated PPG sensor, for instance. Using the smartphone as a physiological sensor unit carries the advantage that the user is well familiar with using a smartphone and no need for additional devices or units of hardware arises. In an alternative embodiment, the physiological sensor unit can of course also be integrated within the breast shield arrangement or another element of the system.

In an embodiment the system further comprises a breast pump. The breast pump comprises a pressure source in air-ducting connection to the breast shield for generating increased or reduced pressure in the breast shield to extract breast milk, and a control unit for controlling the pressure source on the basis of the physiological reception signal from the physiological sensor unit.

Since the pressure source is controlled on the basis of the physiological reception signal, which in turn allows an accurate determination of the MER, frequency and vacuum strength of the breast pump can be controlled to more accurately mimic the baby's natural suckling pattern. For instance, after stimulating the nipple with a higher frequency and lower vacuum strength, the MER occurs. Following the MER, milk starts flowing and the baby will suckle with a slower pace and increased vacuum strength. Multiple MERs will occur during a breastfeed and babies are capable of stimulating additional MERs and adjusting the suckling pattern accordingly. Using the physiological reception signal for controlling the pressure source, a more natural operation of the breast pump can thus be achieved.

In an embodiment the system further comprises a signal processing unit for analysing the physiological reception signal and to generate an according feedback signal for adjustment of the function of the pressure source based on the analysis of the physiological reception signal.

In an embodiment the signal processing unit is configured to analyse AC and DC components of the physiological reception signal, in particular of a PPG sensor or a rPPG sensor, and to evaluate the DC component of the physiological reception signal comprising information on the change of bulk absorption in the breast, in particular on the increase of fluid due to the MER in the breast, and generate an according feedback signal for adjustment of the function of the pressure source.

The DC component of the signal is easy to obtain from the reception signal and can be analysed by simple means.

In an embodiment the signal processing unit is configured to detect the increase of fluid in the breast by comparison of the value of the DC component to a predetermined threshold value.

The threshold values can be chosen from calibration measurements or from medical evaluations over certain shares of the female population.

Additionally or alternatively, an increase about a certain percentage, for instance of about 5%, can be accounted to an increase of fluid in the breast and thus to the occurrence of an MER. Additionally or alternatively, user and/or circumstance specific boundaries, for instance taking into account breast size, more/less milk expression, etc., can be taken into account. However, these options are of course only examples for determining an adequate threshold or classification for detecting MER, and other implementations are likewise contemplated by the skilled person.

In an embodiment the signal processing unit is further configured to evaluate the AC component of the physiological reception signal comprising information on vital signs, in particular on the heart-rate. The vital signs can be used to control the mental state of the user and in case of need a recommendation or helpful advice can be generated on base of the vital signs.

In an embodiment the system further comprises a user interface for conveying information, guidance and recommendations to the user of the system. This can especially be helpful if the user is in a hurry, insecure or suffers from pain when using the breast pump. Any of these obstacles can be for example relieved by guidance to controlled breathing and thus finding into a state of relaxation supporting the triggering of the milk ejection reflex and the effective emptying of the breast.

Preferably, the user interface is integrated with the physiological sensor unit in the smartphone. Due to the versatility of the smartphone, a user interface with almost no limitations can be provided. Further, due to the wide availability of smartphones, no dedicated user interface device, including additional hardware costs, has to be provided.

In an embodiment the signal processing unit is configured to evaluate an AC component of the reception signal comprising information on vital signs, in particular on the heart-rate, wherein the signal processing unit is further configured to generate a feedback signal containing the heart-rate information contained in the AC component and/ or recommendations or guidance based on the analysis of the heart-rate information of the AC component and to transmit the feedback signal to the user interface.

In an embodiment the system further comprises a determination correction unit for correcting the determination of the MER based on feedback provided by the user.

While the determination of the MER can be very accurate for a large percentage of the population, it can nevertheless be not accurate or not working at all for particular individuals. In this embodiment, based on feedback provided by the user, the system can be taught the occurrence of MER for the individual user and correct the determination based on the provided feedback. Preferably, when the user sees the milk flowing, feedback can be input to, for instance, the user interface, such as by pressing a button and the like. Thereby, MER determination can be provided more accurately for all individuals.

In a further aspect a method for determining an MER is provided. The method comprises attaching a breast shield arrangement on a first breast of a female, receiving a physiological reception signal from the second breast, which is opposite to the first breast, wherein the physiological reception signal is indicative of fluid contents in the second breast, and determining an MER based on a change in fluid contents in the second breast.

The breast shield arrangement can be any kind of breast shield arrangement known in the art, for instance a breast shield arrangement to be used with a breast pump or a breast shield arrangement to be used for breastfeeding, such as for protecting the female's nipples.

The method according to the invention can advantageously be combined with any of the embodiments described with respect to the system above. Advantageously, MER using this method can be determined independent from the use of the system, such as while a baby is breastfeeding. Since MER is determined based on physiological reception signals obtained from the second breast and since no mechanical motion on the first breast negatively influences the reception signal obtained from the second breast, MER can be determined with high accuracy.

In a further aspect a computer program for determining an MER is provided. The computer program comprises program code means for causing a processing unit to receive a physiological reception signal from a second breast of a female, wherein the second breast is opposite to a first breast of which milk is expressed, wherein the physiological signal is indicative of fluid contents in the second breast, and determine an MER based on an analysis of the fluid contents in the second breast.

Preferably, the computer program can be downloadable, such as via an App store or the like, and be executed on a smartphone of the user. However, also other means of distribution, storage, and so on are obvious to a skilled person. In a preferred embodiment, the computer program comprises additional program code means for controlling a function of a breast pump in response to the physiological reception signal. Thereby, operation of the breast pump can be improved, without the mother needing to focus on the expression and taking action herself.

It shall be understood that the system of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
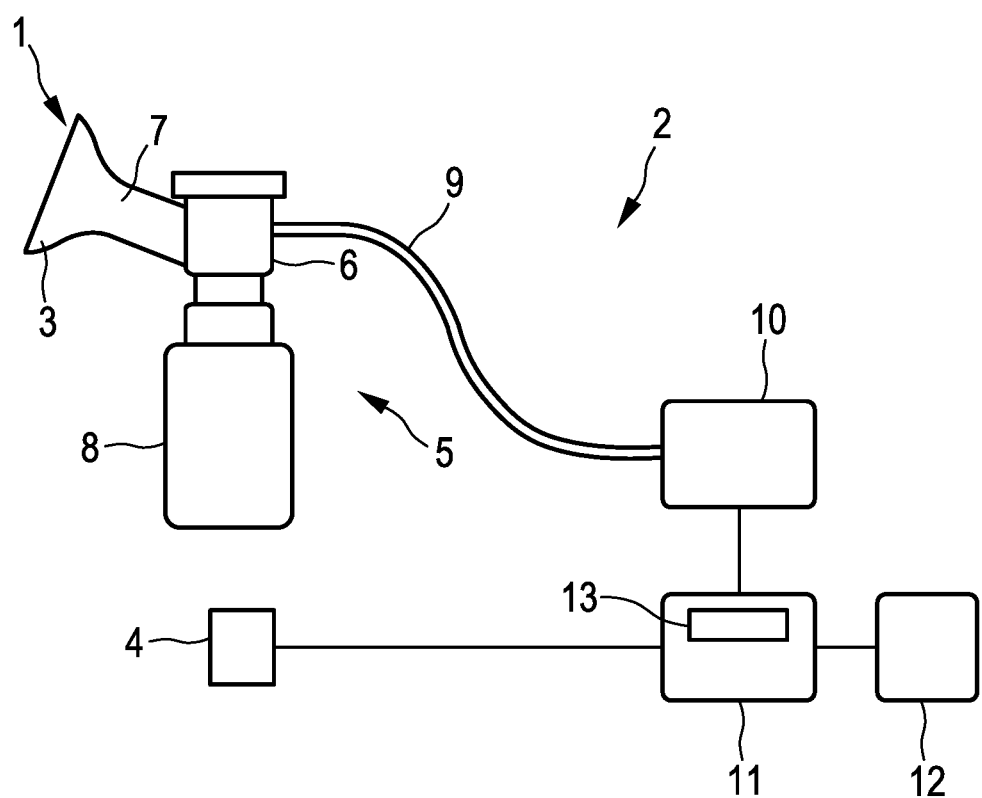
FIG. 1 shows schematically and exemplarily an embodiment of a system comprising a breast pump arrangement according to the invention, FIGS. 2A and 2B schematically and exemplarily show two arrangements of a sensor unit in a system according to the invention.

FIG. 1 shows schematically and exemplarily a first embodiment of a system 100 for milk ejection reflex (MER) determination according to the invention. System 100 comprises a breast shield arrangement 1 for a breast pump 2. The breast shield arrangement 1 comprises a funnel shaped breast shield 3 which is configured to receive a user's breast therein. The breast shield 3 can be formed from any suitable resilient material like polyurethane or silicone. Since breast shields 3 are commonly known in the art, further detailed descriptions about general form and function are deemed to be not necessary here.

According to the invention, system 100 comprises a physiological sensor unit 4 which is arranged for transmitting an input signal into the non-lactating breast, i.e. the breast opposite to the breast the breast shield 3 is to be attached to, and for receiving a corresponding physiological reception signal in response. Exemplary implementations of physiological sensor unit 4 will be explained below with reference to FIGS. 2A and 2B.

Breast shield arrangement 1 is connected to an expression kit 5 via a connecting end 7. The expression kit 5 comprises a receptacle 6, to which the breast shield 3 is connected. The receptacle 6 is configured to receive the milk expressed from the user's breast and to guide it towards a container 8 which is also connected to receptacle 6. In receptacle 6 further components can be housed which are necessary for operation of the breast pump, e.g. a valve assembly (not shown) which allows controlled suction functionality.

The breast pump 2 further comprises an air-ducting connection 9 to a vacuum source 10. The vacuum source 10, used in this embodiment as one exemplary embodiment of a pressure source, is configured to apply negative pressure to breast shield 3 aided by the at least one valve assembly in receptacle 6. Alternatively, the at least one valve assembly can be arranged in a housing of vacuum source 10 or in air-ducting connection 9.

The vacuum source 10 can be any suitable pumping mechanism like a mechanical or an electrical pump.

The breast pump 2 further comprises a control unit 11 in operative interaction to vacuum source 10. The control unit 11 is responsible for the control of the function of vacuum source 10, preferably in dependency from signals received from physiological sensor unit 4 with respect to the non-lactating breast.

Preferably, the breast pump further comprises a signal processing unit 13, e.g. as part of the control unit 11 (as shown in FIG. 1) or as a separate component. Preferably, signal processing unit 13 receives the signals from physiological sensor unit 4, evaluates the information contained therein and generates feedback signals for the adaptation of the function of the vacuum source.

Further, a user interface 12 which can be any or a combination of a speaker, a vibrational signal unit or an optical display may be provided in connection with the control unit 11. The user interface 12 conveys information to the user of system 100 as described later in more detail.

Figure 2A:
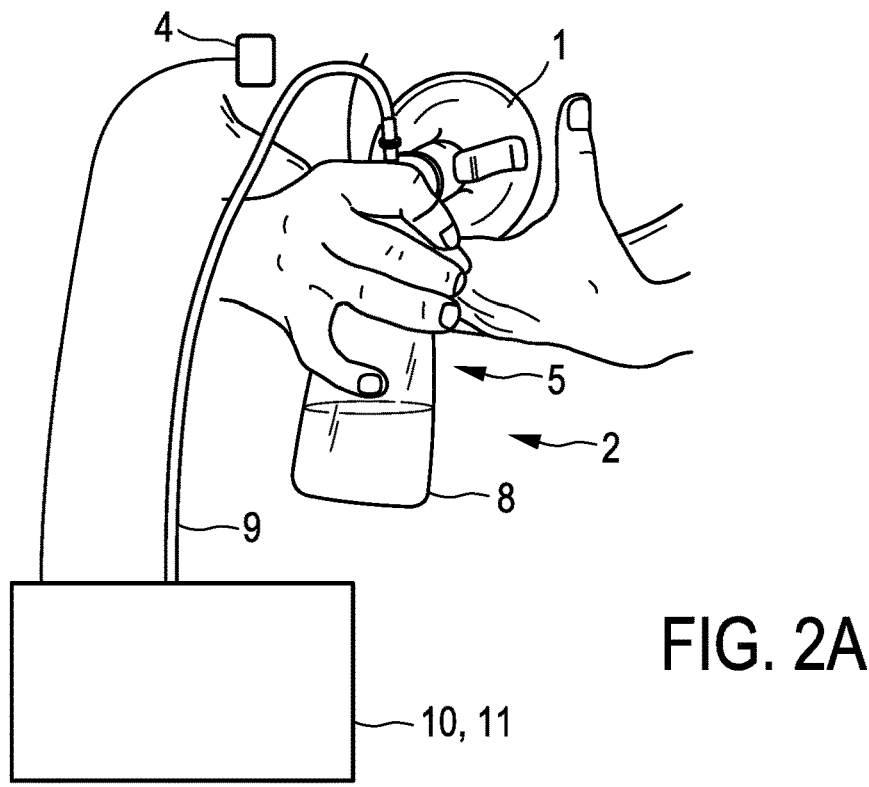
Figure 2B:
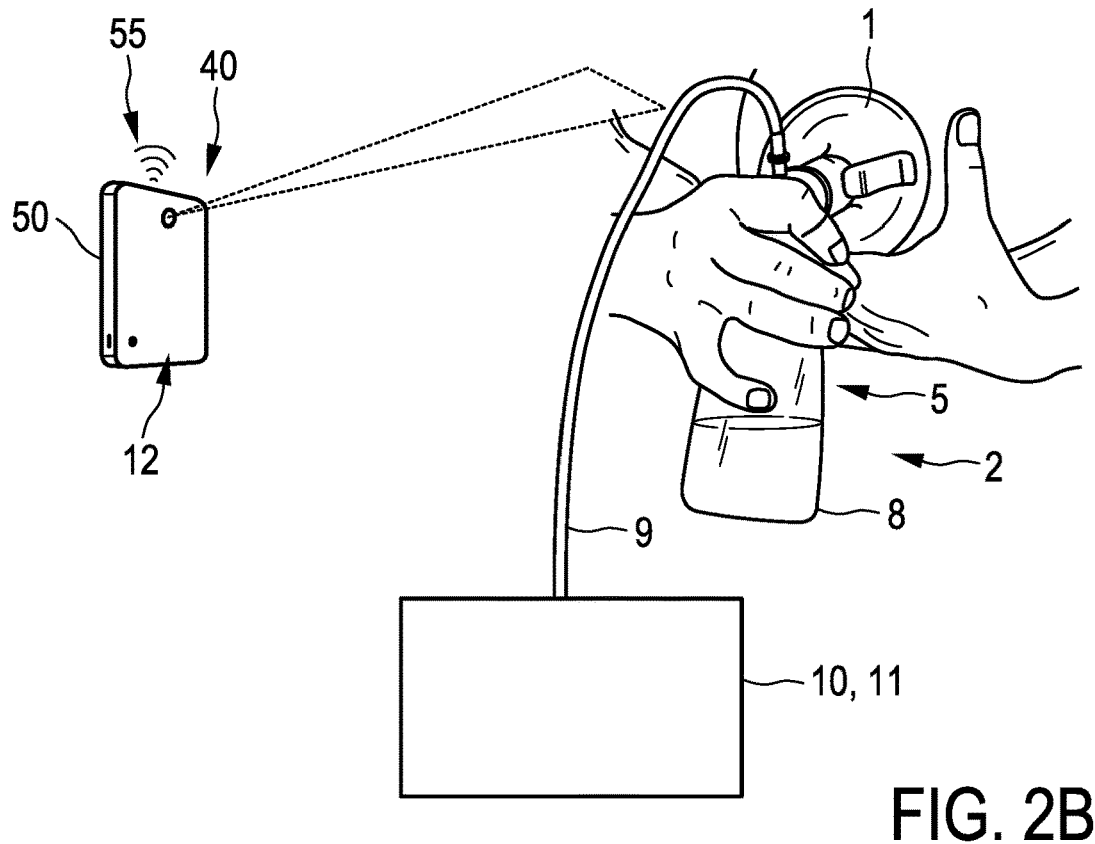

Turning now to FIGS. 2A and 2B, two embodiments of physiological sensor unit 4 of system 100 are illustrated. In FIG. 2A, physiological sensor unit 4 comprises a PPG sensor which is brought into contact with the non-lactating breast, i.e. the breast opposite to where the breast shield 3 is attached to. The illustrated PPG sensor is linked to control unit 11 through a wire, wherein also wireless connections are contemplated in other embodiments. The occurrence of the milk ejection reflex (MER) is in this embodiment obtained from the PPG sensor signal and will preferably trigger the change in the setting of breast pump 2 for the breastfeeding breast, i.e. changing between the suckling pattern from "triggering" to "emptying". The PPG sensor preferably comprises one LED, while in other embodiments multiple LEDs with a combination of different wavelengths preferably in the range between 400 nm and 1300 nm is employed.

FIG. 2B schematically and exemplarily illustrates another embodiment, in which physiological sensor unit 4 comprises a camera 40 for obtaining a physiological signal, preferably a remote PPG (rPPG) signal of the non-lactating breast. Camera 40 may be an external camera included in a smartphone 50 or the like, or a camera integrated in, for instance, breast shield 3 of system 100. Preferably, the rPPG signal is then extracted from the recording image of the non-lactating or non-breastfeeding breast. To this end, preferably an algorithm is provided for recognizing the breast pump head and/or a baby for distinguishing the breastfeeding breast from the non-breastfeeding breast. Preferably, breast pump 2 can emit a signal, e.g. light, which facilitates distinguishing the breastfeeding from the non-breastfeeding breast by the algorithm.

In the example of FIG. 2B, user interface 12 is also integrated into smartphone 50. To this end, smartphone 50 communicates with control unit 11 of system 100 via a wireless connection 55.

While with reference to FIGS. 2A and 2B PPG signals obtained by physiological sensor unit 4 are disclosed as exemplary physiological signals, in other embodiments, different techniques can be used to detect a physiological signal which leads to the determination of an MER. Such further techniques may be contact based, such as bio impedance, laser speckle and thermal sensing. Additionally or alternatively, the technique can be non-contact based, including laser speckle imaging and thermal imaging. In this embodiment, the entire control of breast pump 2 can be integrated into an App running on smartphone 50, for instance. Physiological sensor unit 4 can thus, dependent on the measuring principle, determine the physiological reception signal directly, such as in the case of thermal sensing, or after and depending on the transmission of an input signal into the non-lactating breast, such as in the case of PPG.

While system 100 has been described comprising a single breast shield 3, in other embodiments, also one breast shield 3 and a corresponding pump arrangement for both breasts can be contemplated. In this embodiment, preferentially the breasts are alternatively subjected to vacuum from vacuum source 10 and the physiological sensor unit 4 inputs the signal into the opposite breast, respectively. Accordingly, accurate MER determination can be performed even in case both breasts are used for milk expression. For example, a physiological sensor unit 4 might be arranged on an inner or outer surface of each of the two breast shields 3, respectively.

For the embodiment of two breast shields 3, which are to be attached to opposite breasts, also a single physiological sensor unit 4, such as the exemplary camera 40 comprised in smartphone 50 can be employed.

Alternatively or additionally, two physiological sensor units 4 directed each to one of the two breasts can be employed and, for instance, provided with each of the two breast shields 3. Then, the respective physiological sensor can either transmit the input signal into the breast the respective breast shield 3 is attached to, or into the opposite breast. Dependent thereon, each of the physiological sensors will either operate together with the breast pump 2 of the corresponding breast shield (i.e. in case physiological sensor directed to opposite breast) or contracyclical, i.e. in case the respective breast pump 2 is not operating (i.e. in case physiological sensor directed to same breast).

In case physiological sensor unit 4 comprises an optical sensor, arrangement on the outer surface is thus possible when the material of breast shield 3 is translucent, or if each physiological sensor is directed towards the opposite breast. Arrangement on the outside would be preferable since the danger of injury of the user or of damage of the physiological sensor is minimized.

Alternatively the physiological sensor can also be embedded in the material of the breast shield 3. "Embedded" in this respect is meant to describe an arrangement of the physiological sensor either in a recess of the breast shield 3 wherein the recess is open to at least one surface of the breast shield 3, or completely covered with the breast shield's material. The latter could for example be accomplished by moulding or casting.

In case the physiological sensor is arranged on an inner surface of the breast shield 3, it comprises preferably a sensor pad which surrounds the physiological sensor and spaces the physiological sensor from the skin of the user. The background of this additional sensor pad is the observation, that a physiological sensor which is directly placed on the user's skin might lead to biased measurement values due to the pressure of the physiological sensor on the skin. The thickness of the sensor pad should be sufficiently small to make sure that the physiological sensor remains in close proximity of the skin of the user. Preferably, the distance between the physiological sensor and the skin of the user is less than 1 cm, particularly preferable less than 0.5 cm. It should be noted that the respective physiological sensor is only operated as long as the particular breast it is sensing is not subjected to vacuum pressure, e.g. by vacuum source 10.

As indicated, the physiological sensor unit 4 preferably comprises an optical sensor, especially a photoplethysmographic (PPG) sensor. PPG sensors are known in the arts, they are especially used for measurement of the oxygen saturation of the blood. To facilitate the understanding of the invention, the measurement principle of a PPG sensor is shortly described in the following.

At least one light source, for example a light emitting diode, emits light which is introduced into the tissue of the respective body part. Normally, for measurement a thin part of the body like a finger tip or the earlobe is used. In these cases, the light from the light source passes through the whole body part's tissue and is detected by at least one photodetector which is arranged opposite to the light source with the body part between light source and detector. The amount of light transmitted through the tissue is measured by the photodetector and compared to the emitted light from the light source. The difference between the values is a measure for the bulk absorption and the fluid contents of the respective tissue. From this, the degree of oxygen saturation in the blood which flows through the tissue can be calculated. If the saturation is higher the amount of transmitted light will be different compared to a lower saturation due to differences in the bulk absorption and the fluid contents.

In case of the system 100 including breast shield arrangement 1 and breast pump 2 described above, it is not possible to transmit light through the breast tissue to a detector which is arranged opposite to the light source, since the amount of tissue is too large to be rayed completely. In this case, the light is emitted into the tissue and the amount of light reflected in the tissue is measured by the detector. The physiological sensor unit 4 thus preferentially comprises at least one light source and at least one photodetector adjacent to each other with the light source sending light into the breast tissue and the detector detecting the amount of light reflected in the breast tissue.

Accordingly, the amount of reflected light will vary with varying degree of fluid contents in the breast tissue. On the one hand, the breast tissue is supplied with blood, on the other hand the breast tissue of women, who have born recently, produces breast milk enabling the women to feed their children by breastfeeding. Thus, a milk flow in the breast tissue will be detectable by a change in fluid contents of the breast tissue.

To start milk ejection from the breast, the so-called milk ejection reflex (MER) has to be triggered. Triggering normally works by suckling action of the child on the nipple of the feeding woman. By this suckling action, the hormone oxytocin is emitted into the blood and triggers milk ejection when detected by receptor cells in the breast tissue. In case of a nursing woman, the milk ejected from the breast leads to a different suckling action of the child. If a nursing mother is forced however to refrain from breastfeeding and instead has to collect breast milk by a breast pump 2, the milk ejection normally has to be monitored by the user of the breast pump 2 directly. The state of the art only offers breast pumps which detect the presence of milk flow outside the breast tissue. In these breast pumps, erroneous measurements and delays in adaptation of the functionality of the breast pump are observed.

The breast pump 2 according to the invention offers by use of the physiological sensor unit 4 a direct detection of the start of the milk ejection in the breast tissue even before the milk ejection outside the breast is detected. Thus, the pressure source 10 can react directly on the start of the milk expression. The breast pump 2 is operated at a certain suction pressure and suction frequency until the milk ejection is detected by the physiological sensor unit 4. The signal received due to the change in fluid contents in the breast tissue is sent to the control unit 11, analysed by the signal processing unit 13 and fed back to the vacuum source 10 to change the suction modus.

For the analysis of the signals, a known technique is used. The signal detected by the photodetector is split up in two components, the AC component and the DC component and the different components analysed on the information contained therein. A schematic diagram of the components is shown for reference in FIG. 3.

Figure 3:
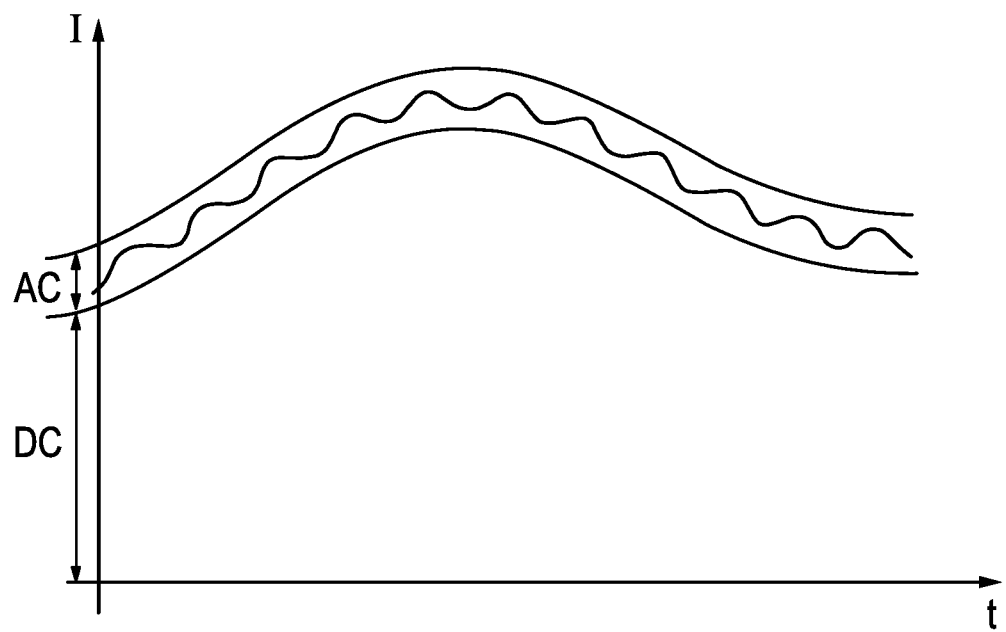
FIG. 3 shows schematically and exemplarily a diagram of the AC and DC components of the signal derived from an optical sensor in a system according to FIG. 1 or 2.

FIG. 3 shows schematically and exemplarily a typical signal sequence, for instance of a PPG signal, comprised of an AC and a DC. The AC component mainly contains information on vital signs, especially on the heart rate. The DC component contains information on the bulk reflection in the breast tissue. The ratio AC/DC is called the modulation and reflects, as a percentage, the amount which can be used for derivation of the heart rate.

For the inventive system 100 comprising the breast shield arrangement 1 for a breast pump 2, the DC component is the relevant measure. When the milk ejection starts, the fluid content in the breast tissue increases compared to the normal status when the breast tissue is only supplied with blood. The increase in signal reflects the presence of both fluids, namely blood and milk.

Figure 4:
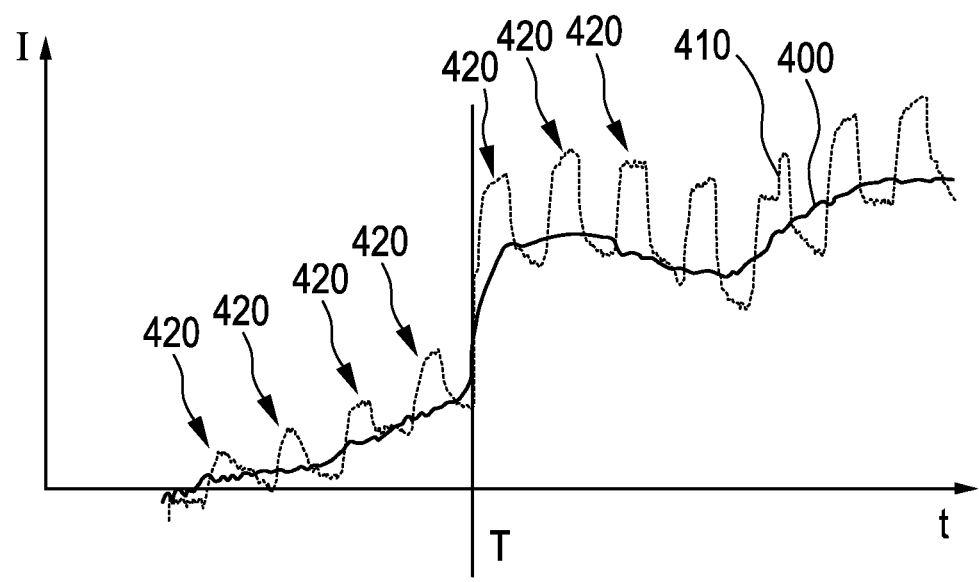
FIG. 4 shows schematically and exemplarily a diagram of the physiological signal indicative of MER in a female breast.

FIG. 4 schematically and exemplarily illustrates the detectable increase in DC component, wherein the advantageous effect of determining the physiological signal from the non-lactating breast is clearly visible. FIG. 4 illustrates signal sequence 400 originating from physiological sensor unit 4. For comparison, a signal sequence 410, which would have been obtained at the same time from the lactating breast is also illustrated. The intensity of the respective physiological signal is denoted as I on the vertical axis, while time is denoted on the horizontal axis. A clear increase in DC component of signal sequence 400 can be seen at time T. This increase is the change in fluid contents in the breast tissue and the different absorption of light resulting there from. This jump in signal sequence 400 is detectable by physiological sensor unit 4 and can be used to control the suction mode or pattern of vacuum source 10, for instance.

The advantage of using the non-lactating breast compared to the lactating breast becomes evident by analyzing signal sequence 410 in further detail. The cycles of the vacuum source 10 have an influence on the intensity of the physiological signal, expressed by periodic peaks 420 of signal sequence 410. The noise created by the breast pump leading to peaks 420 can be larger than the DC jump accountable to the MER, making it difficult to detect MER when physiological sensor unit 4 would determine the physiological reception signal from the lactating breast. Instead, as can be seen in signal sequence 400, the physiological reception signal of the non-breastfeeding or non-lactating breast leads to a cleaner signal due to the absence of noise. In one example, MER can be detected by using a boundary or threshold, which has to be exceeded in absolute value or change of absolute value of the DC component. For example, an increase of the DC value by 5% and/or by using user or circumstance specific boundaries can be employed. User specific values and/or circumstances can include, for instance, the breast size or calibration measurements from earlier pumping cycles, reference subjects, and so on.

Preferentially, in case an MER is determined, the operation of breast pump 2 is automatically controlled. Thus, the user of breast pump 2 has no necessity to act on her own account when she feels that milk expressions started, but simply relies on the automated action of breast pump 2 in reaction to the determined MER.

The physiological sensor unit 4 does not necessarily have to comprise a normal PPG sensor, but can also be a remote PPG sensor which also works from a certain distance, for instance implemented as a camera 40 of smartphone 50. Additionally or alternatively, physiological sensor unit 4 can also comprise a contact or imaging laser-speckle interferometer, a contact or imaging biothermal sensor, a bioimpedance sensor or a further suitable technique for determining a physiological signal of which the MER can be determined.

Preferably, the relevant value—the increase in the DC component—is however present in the values of the sensor types referred to.

As already mentioned with reference to FIG. 1, a user interface 12 can be present, which is connected to the control unit 11. The user interface 12 can comprise for example a speaker, a vibrational unit and/or a display. The user interface 12 is suitable to convey information to the user of the breast pump 2, especially information derived from the above-mentioned AC component of the signal detected by the physiological sensor unit 4. The AC component of the signal comprises mainly information on the vital signs of the user, for example the heart rate, and can be used to generate a feedback for stress relaxation. In an advantageous implementation, user interface 12 can be integrated into a smartphone and be wirelessly connected to the control unit 11.

Young women nourishing for the first time often are insecure and nervous when using a breast pump 2. Thus, the heart rate of these users will be high and reflect their mental state. On the other hand, this nervousness might lead to bad results when trying to extract breast milk from the breast. The signal processing unit 13 of the control unit 11 can analyse the AC component of the signal in addition to the DC component and convey useful information contained therein via the user interface 12 to the user. For example, it is possible that a recommendation is generated and presented to the user to help to decrease the heart rate by a special breathing technique. If the breathing technique is successful, the decrease in heart rate is also fed back to the user thus improving the comfort and ease of the user. Stress relaxation generally will help to increase the flow of breast milk and thus can improve the yield.

To further improve the precise function of the breast pump 2 it is possible to arrange a second sensor, e.g. in form of a flow sensor, for example in the expression kit 6 or in the air-ducting connection 9. By way of the flow sensor, an additional measure about the time and amount of milk extraction from the breast can be gained and used to control the functionality of the breast pump 2, for instance by generating a control signal for the breast pump based on the reception signal of the physiological sensor unit 4 and the signal from the additional flow sensor.

Yet another implementation of the invention is the application of the sensor in combination with a positive pressure pump instead of a vacuum pump applying negative pressure or suction to the breast. Although this may require a different connection of the air ducting to the breast shield, the sensor provided according to the invention can be used with the same or similar measurement function and with similar results.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for milk ejection reflex determination, comprising:
   a breast shield arrangement for a breast pump configured for attachment to a first lactating attached breast of a female,
   a physiological sensor unit configured to receive a physiological reception signal from a second non-lactating breast of the female not attached to the breast shield arrangement,
   wherein the physiological reception signal is indicative of fluid contents in the second non-lactating breast of the female not attached to the breast shield arrangement, and
   wherein the system is configured to determine a milk ejection reflex based on a detected change in the fluid contents in the second non-lactating breast of the female not attached to the breast shield arrangement prior to breast milk becoming detectable outside of breast tissue of the second non-lactating breast of the female not attached to the breast shield arrangement.

2. The system according to claim 1, wherein the physiological sensor unit comprises a contact photoplethysmographic sensor, configured to be arranged in contact with the skin of the second non-lactating breast of the female not attached to the breast shield arrangement or in close proximity to the skin of the second non-lactating breast of the female not attached to the breast shield arrangement.

3. The system according to claim 1, wherein the physiological sensor unit comprises a remote photoplethysmographic sensor.

4. The system according to claim 3, wherein the physiological sensor unit comprises a camera.

5. The system according to claim 3, wherein the physiological reception sensor unit is disposed to be at a distance of less than 1 cm from the second non-lactating breast of the female not attached to a breast shield arrangement.

6. The system according to claim 1, wherein the physiological sensor unit comprises a laser speckle imaging sensor.

7. The system according to claim 1, wherein the physiological sensor unit comprises a thermal sensor.

8. The system according to claim 1, wherein the physiological sensor unit comprises a bio impedance sensor.

9. The system according to claim 1, wherein the physiological sensor unit is integrated into a smartphone.

10. The system according to claim 9, wherein the smart phone inlcudes a dedicated physiological sensor unit.

11. The system according to claim 1, further comprising a breast pump comprising:
    a pressure source in air-ducting connection to the breast shield, the pressure source configured to generate one of increased or reduced pressure in the breast shield to extract breast milk, and
    a control unit configured to control the pressure source on the basis of the physiological reception signal received from the physiological sensor unit.

12. The system according to claim 11, further comprising a signal processing unit programmed to analyze the physiological reception signal and generate therefrom a feedback signal adjusting the pressure source based on the analysis of the physiological reception signal.

13. The system according to claim 12, wherein the signal processing unit is configured to analyze an AC signal component and a DC signal component of the physiological reception signal and evaluate the DC signal component of the physiological reception signal comprising information on the change of bulk absorption in the second non-lactating breast of the female not attached to the breast shield arrangement indicative of an increase of fluid due to the milk ejection reflex in the second non-lactating breast of the female not attached to the breast shield arrangement, and generate a feedback signal adjusting the pressure source.

14. The system according to claim 13, wherein the signal processing unit is configured to detect the increase of fluid in the second non-lactating breast of the female not attached to the breast shield arrangement by comparing a value of the DC signal component to a predetermined threshold value.

15. The system according to claim 13, wherein the the physiological reception signal is one of a photoplethysmography sensor or a remote photoplethysmography sensor.

16. The system according to claim 1, further comprising a user interface configured to convey at least one of information, guidance and recommendations directed to controlling a mental state of the female.

17. The system according to claim 16,
wherein the signal processing unit is configured to:
evaluate the AC signal component of the physiological reception signal comprising vital sign information, and
generate a feedback signal including the vital sign information and/or one of recommendations and guidance based on the analysis of the vital sign information and transmit the feedback signal to the user interface.

18. The system according to claim 16, wherein the vital sign includes heart rate information.

19. A method for determining a milk ejection reflex, the method comprising:
attaching a breast shield arrangement on a first lactating attached breast of a female,
receiving a physiological reception signal from a second non-lactating breast of the female not attached to the breast shield arrangement,
wherein the physiological reception signal is indicative of fluid contents in the second non-lactating breast of the female not attached to the breast shield arrangement, and
determining a milk ejection reflex based on a detected change in fluid contents in the second non-lactating breast of the female not attached to the breast shield arrangement as indicated by the physiological reception signal.

20. A computer program for determining a milk ejection reflex, the computer program comprising program code means for causing a processing unit to:
receive a physiological reception signal from a second non-lactating breast of a female not attached to a breast shield arrangement, wherein the second non-lactating breast of the female not attached to the breast shield arrangement is opposite a first lactating attached breast of the female from which milk is expressed via attachment to the breast shield arrangement,
wherein the physiological reception signal is indicative of fluid contents in the second non-lactating breast of the female not attached to a breast shield arrangement, and
determine a milk ejection reflex based on an analysis of the physiological reception signal.

\* \* \* \* \*